United States Patent [19]

Sweet et al.

[11] Patent Number: 6,022,522
[45] Date of Patent: Feb. 8, 2000

[54] RIGID BIFUNCTIONAL CHELATING AGENTS

[75] Inventors: Mark P. Sweet, Coram, N.Y.; Ronnie C. Mease, Fairfax, Va.; Suresh C. Srivastava, Setauket, N.Y.

[73] Assignee: Brookhaven Science Associates, Upton, N.Y.

[21] Appl. No.: 09/046,030

[22] Filed: Mar. 23, 1998

Related U.S. Application Data

[62] Division of application No. 08/506,889, Jul. 26, 1995.

[51] Int. Cl.[7] .......................... A61K 51/00; A61M 36/14
[52] U.S. Cl. .......................... 424/1.49; 534/14; 424/1.11; 424/1.53
[58] Field of Search .................................. 424/1.11, 1.49, 424/1.53, 1.65, 1.69, 9.1, 130.1; 534/7, 10–16

[56] References Cited

U.S. PATENT DOCUMENTS 5,783,169  7/1998  Sweet et al. ........................ 424/1.65

*Primary Examiner*—Jose' G. Dees
*Assistant Examiner*—Dameron Jones
*Attorney, Agent, or Firm*—Margaret C. Bogosian

[57] ABSTRACT

Bicyclo[2.2.2]octane-2,3 diamine-N,N,N',N'-tetraacetic acids (BODTA) and bicyclo[2.2.1]heptane-2,3 diamine-N,N,N',N'-tetraacetic acid (BHDTA) are chelating agents useful in forming detectably labeled bioconjugate compounds for diagnostic and therapeutic purposes. New compounds and processes of forming BODTA and BHDTA are disclosed. Radioimmunoconjugates of the present invention show high and prolonged tumor uptake with low normal tissue uptakes.

1 Claim, 7 Drawing Sheets

DCC = DICYCLOHEXYLCARBODIIMIDE
NHS = N-HYDROXYSUCCINIMIDE
DMSO = DIMETHYLSULFOXIDE
DCU = DICYCLOHEXYL UREA

RIGID BIFUNCTIONAL CHELATING AGENTS

This is a divisional of copending application Ser. No. 08/506,889 filed Jul. 26, 1995.

This invention was made with Government support under contract number DE-AC02-76CH00016, between the U.S. Department of Energy and Associated Universities, Inc. The Government has certain rights in the invention.

BACKGROUND OF THE INVENTION

The present invention relates to new rigid chelating structures, methods for preparing the structures and their use in preparing radioimmunoconjugates for SPECT and PET imaging and for radiotherapy.

The use of radiometals to label proteins and antibodies provides a variety of choices of half-life and types of emission(s) for various medical applications in both diagnosis and therapy. Radiometals also offer significant advantages over iodine when used to label monoclonal antibodies. Radiometal labeling, for example, avoids the deleterious effects of oxidation experienced in direct iodination reactions. Labeling with metals can also overcome problems of in vivo deiodination by tumor and normal tissues, particularly when using rapidly internalized antibodies.

Radiometals can generally be attached to antibodies by the use of a "bifunctional chelate" which is first covalently attached to the antibody to form an antibody-chelate conjugate and then bound to the radiometal. The early work in this field used diethylenetriaminepentaacetic acid (DTPA) and its derivatives. This compound has a backbone consisting of three nitrogens separated by two ethylene bridges. The two terminal amine groups each contain two carboxymethyl groups while the internal amine contains one carboxymethyl group. DTPA is generally conjugated to antibodies via its bicyclic anhydride (DTPADA) which forms a covalent amide bond between an antibody amine and one of the carboxylic acid groups of DTPA [Hnatowich, et al. Science 220, 613 (1983)]. This method while convenient has drawbacks. For example, with indium-ill this procedure yields high liver retention and slow body clearance [Goodwin, J. Nucl. Med. 28, 1358 (1987)], as well as a substantial amount of crosslinked antibody (two antibodies linked together by a DTPA bridge). This crosslinking can reduce the immunoreactivity of the antibody, increase liver retention, and decrease tumor uptake.

One strategy available to overcome the problems caused by liver retention is to use chelates which bind the metal strongly thus forming more stable radiometal complexes. Strong metal-ligand bindings are important because weakly bound metals cause increased radiation dose to normal tissues such as kidneys, bone marrow and liver.

Accordingly, there is still a need in the art of radiolabeling for bifunctional ligands which can bind radiometals very strongly thus avoiding increased radiation dose to normal tissues.

It is, therefore, an object of the present invention to provide a new family of functional chelating agents which can bind radiometals very strongly and are capable of surviving in vivo. Another object of the present invention is to provide rigid bifunctional chelating agents which can be conjugated to monoclonal antibodies and other bioactive molecules and overcome the stability problems associated with other prior art chelating agents.

SUMMARY OF THE INVENTION

The present invention provides rigid chelating structures having a rigid cyclic hydrocarbon backbone. The chelating structures of the present invention include compounds of the formula where X can be hydrogen, amine, isothiocyanate, bromoacetamide, maleimide or derivatives thereof. Strong chelates may be formed with many divalent and trivalent radiometals using the two adjacent nitrogens and the four carboxylic acid groups. The chelates of the present invention contain at least one moiety or a double bond which can be functionalized and/or derivatized for attachment to proteins and other bioactive molecules. Antibody-metal conjugates can be formed by the proper choice of radiometal and antibody.

Radioimmunoconjugates of the present invention show high and prolonged tumor uptake with low retention in normal organs such as kidneys, bones, and liver.

The chelating agents of the present invention are useful for diagnostic procedures including planar imaging, SPECT imaging, PET imaging, as well as in therapeutic procedures.

As a result of the present invention, chelating agents having a rigid backbone are provided which can bind many di-valent and tri-valent radiometals very strongly, thereby keeping the radiometal bound to the antibody which results in decreasing the radiation dose to non-target tissues. Because of their rigid backbone, the chelating agents of the present invention can hold the amino groups in a fixed position, thereby reducing both metal-ligand dissociation and competition for radiometals by other ligands, thus increasing the stability of the resulting conjugate. In contrast, the distance between amino groups in either acyclic or cyclic diamines which undergo changes in conformation is not fixed because the amino groups can rotate about the carbon-carbon bond.

Moreover, the rigid carbon backbone of the chelating agents of the present invention increases the in-vivo kinetic stability of metal-ligand conjugates by sterically hindering the approach of other ligands to the metal.

Additionally, the C-5 double bonds in the bicyclic systems of the present invention can be readily functionalized, thereby enabling the artisan to prepare stable radiometal conjugates with a variety of biologically active molecules such as proteins, antibodies, peptides, enzymes and hormones useful for imaging and/or therapy applications in nuclear medicine. The chelating agents of the present invention can also be used to develop other useful ligands by the ability of being incorporated into macrocyclic ligands such as 1,4,7,10-tetraazacyclododecane N,N',N",N'"-tetraacetic acid (DOTA) and 1,4,8,11-tetraazacyclotetradecane N,N',N",N'"-tetraacetic acid (TETA).

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

DETAILED DESCRIPTION OF THE INVENTION

The present invention provides a new family of bifunctional chelating agents and methods for their preparation. The rigid chelating structures of the present invention contain a rigid cyclic hydrocarbon backbone. Strong chelates can be formed with many divalent and trivalent radiometals using the two amine nitrogens and the four carboxylate groups. The chelates of the present invention contain a moiety or a double bond which can be functionalized and/or derivatized for attachment to proteins and other bioactive molecules. Antibody-metal conjugates are formed by the proper choice of radiometal and antibody. The resulting conjugates can be used for diagnostic imaging or therapy. The present invention also provides methods of use of the chelating agents of the invention for stable attachment of radiometals to biologically active molecules including proteins and antibodies for diagnostic as well as therapeutic applications. More specifically, the present invention provides ligands which contain a rigid carbon backbone and which can form strong chelates with many di-and tri-valent radiometals. The chelating agents prepared according to the present invention include high yields of bicyclo[2.2.2] octane-2,3 diamine-N,N,N',N'-tetraacetic acids (BODTA) and bicyclo[2.2.1]heptane-2,3 diamine-N,N,N',N'-tetraacetic acid (BHDTA).

The chelating agents of the present invention can be synthesized, derivatized, conjugated to antibodies and/or used to chelate radiometals.

Figure 1:
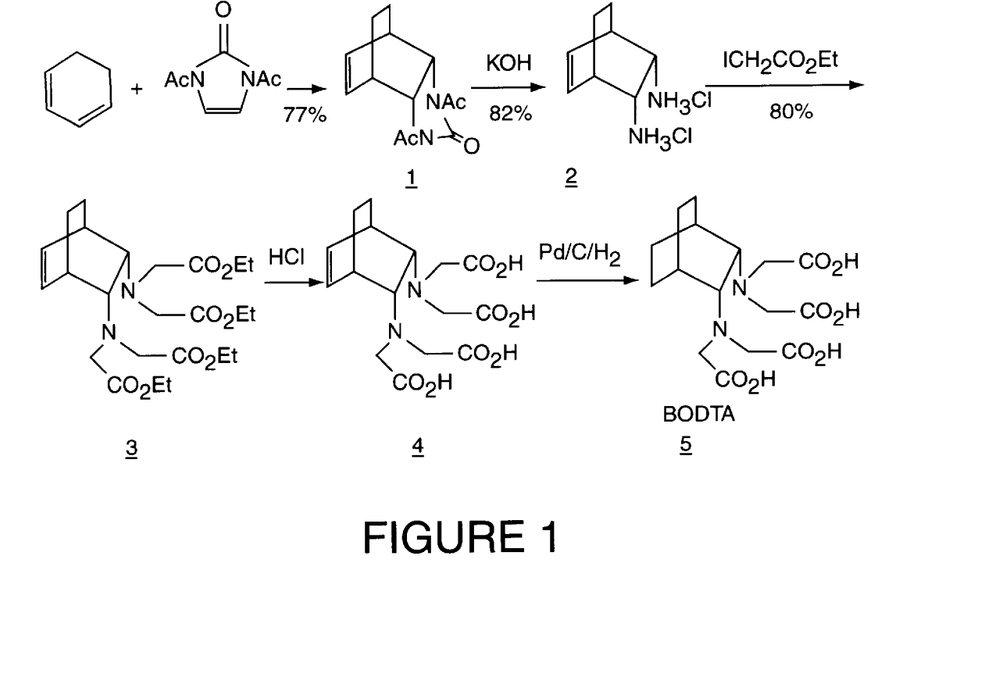
FIG. 1 depicts the synthesis of BODTA.

The synthesis of BODTA is illustrated in FIG. 1, below.

In FIG. 1, 1,3-diacetylimidazolin-2-one and 1,3-cyclohexadiene were added in a Diels-Alder reaction to form 3,5-diacetyl-3,5-diazatricyclo[5.2.2.0]undec-8-en-4-one (compound 1). Mild base hydrolysis of compound 1 resulted in the deacylated product 3,5-diazatricyclo[5.2.2.0] undec-8-en-4-one. Base hydrolysis of 3,5-diazatricyclo [5.2.2.0]undec-8-en-4-one under forced conditions at temperatures from about 155° C. to about 170° C. provided cis-endo-bicyclo[2.2.2]oct-5-ene-2,3 diamine dihydrochloride (Compound 2). Compound 2 was then alkylated with ethyl iodoacetate to provide cis-tetraethyl bicyclo[2.2.2]oct-5-ene-2,3-diamine-N,N,N',N'-tetraacetate (Compound 3). Compound 3 was hydrolyzed to form cis-bicyclo[2.2.2]oct-5-ene-2,3-diamine-N,N,N',N'-tetraacetic acid (Compound 4). Compound 4 was catalytically hydrogenated to form bicyclo [2.2.2]octane-2,3-diamine-N,N,N',N'-tetraacetic acid (BODTA) (Compound 5).

Figure 2:
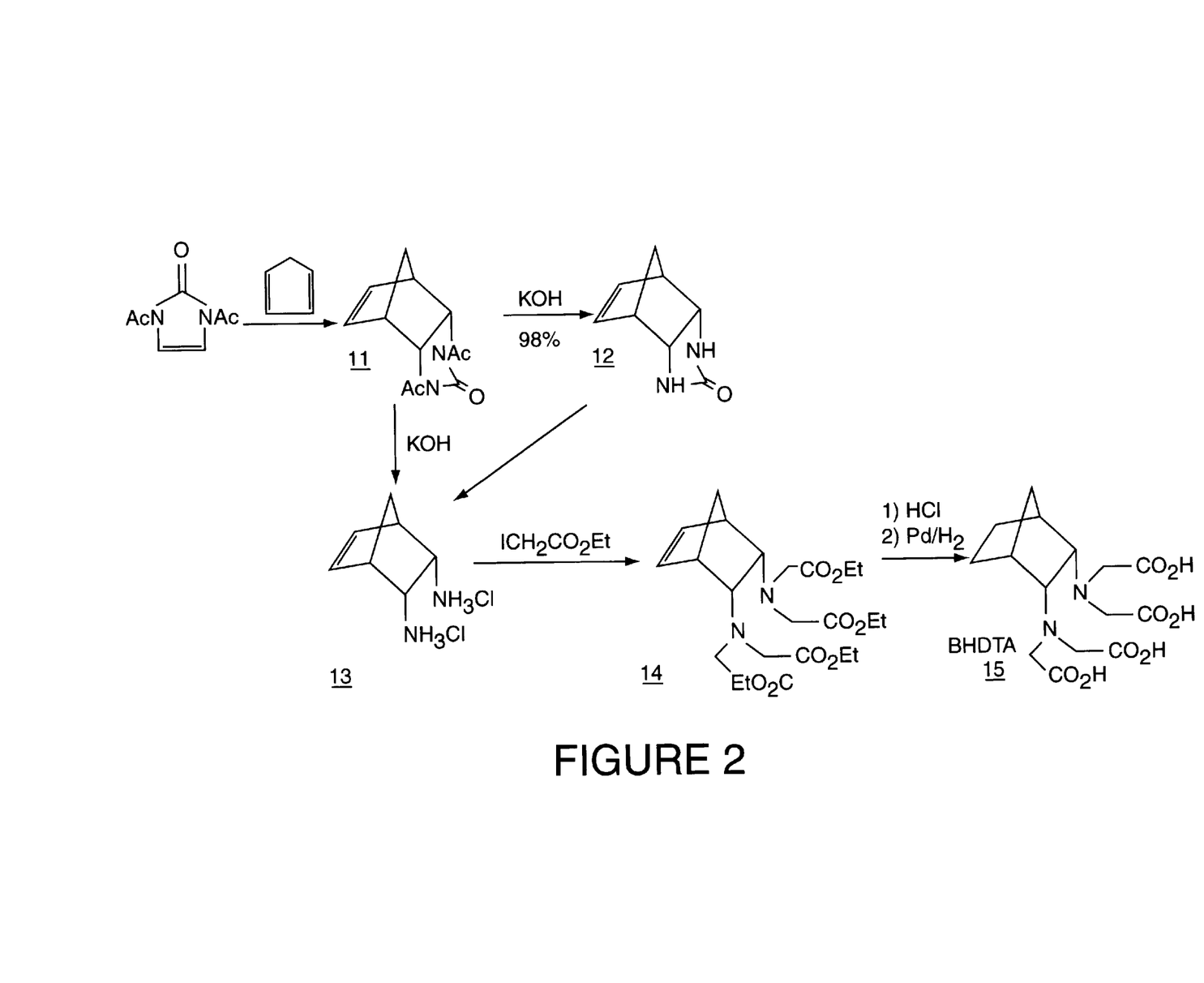
FIG. 2 depicts the steps in the synthesis of BHDTA are similar to those used to synthesize BODTA.

The steps in the synthesis of BHDTA are similar to those used to synthesize BODTA and are illustrated in FIG. 2, below.

In FIG. 2, 1,3-diacetylimidazolin-2-one and 1,3-cyclopentadiene are added in a Diels-Alder reaction to form 3,5-diacetyl-3,5-diazatricyclo[5.2.1.0]dec-8-en-4-one (compound 11). Mild base hydrolysis of compound 11 resulted in the deacylated product 3,5-diazatricyclo[5.2.1.0] dec-8-en-4-one (compound 12). Base hydrolysis of compound 12 under forced conditions provided cis-endo-bicyclo [2.2.1]hept-5-ene-2,3-diamine dihydrochloride (compound 13). Alkylation of compound 13 with ethyl iodoacetate provided cis-tetraethyl bicyclo[2.2.1]hept-5-ene-2,3-diamine-N,N,N',N'-tetraacetate (compound 14). Compound 14 is hydrolyzed and catalytically hydrogenated to form bicyclo[2.2.1]heptane-2,3-diamine-N,N,N',N'-tetraacetic acid (BHDTA).

Figure 3:
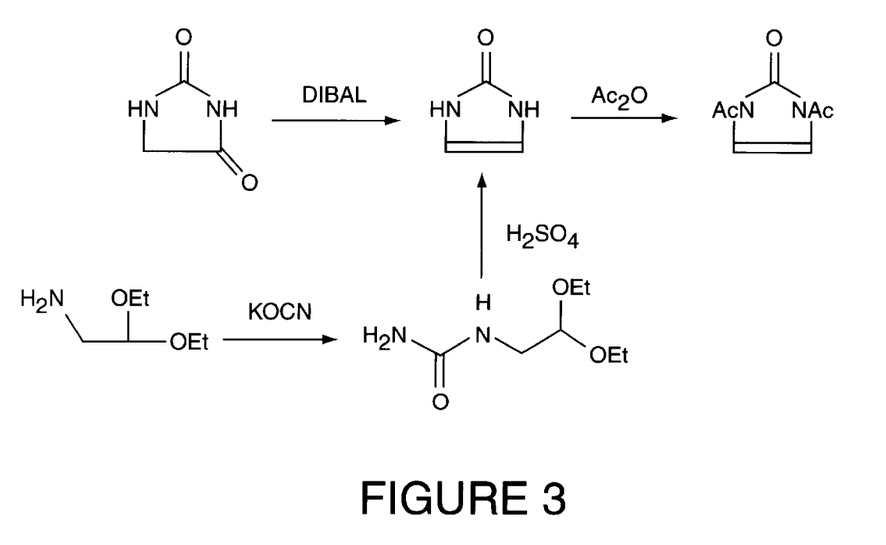
FIG. 3 depicts the preparation of 1,3-diacetyl imidazolin-2-one.

In both FIGS. 1 and 2, the cyclopentadiene and cyclohexadiene are commercially available from Aldrich Chemical Company. 1,3-diacetyl imidazolin-2-one was prepared as shown in FIG. 3 below.

1,3-Diacetyl imidazolin-2-one was formed by the reaction of α-aminoacetaldehyde diethyl acetal and potassium cyanate to form a urea followed by acid catalyzed cyclization and acylation with acetic anhydride.

Figure 4:
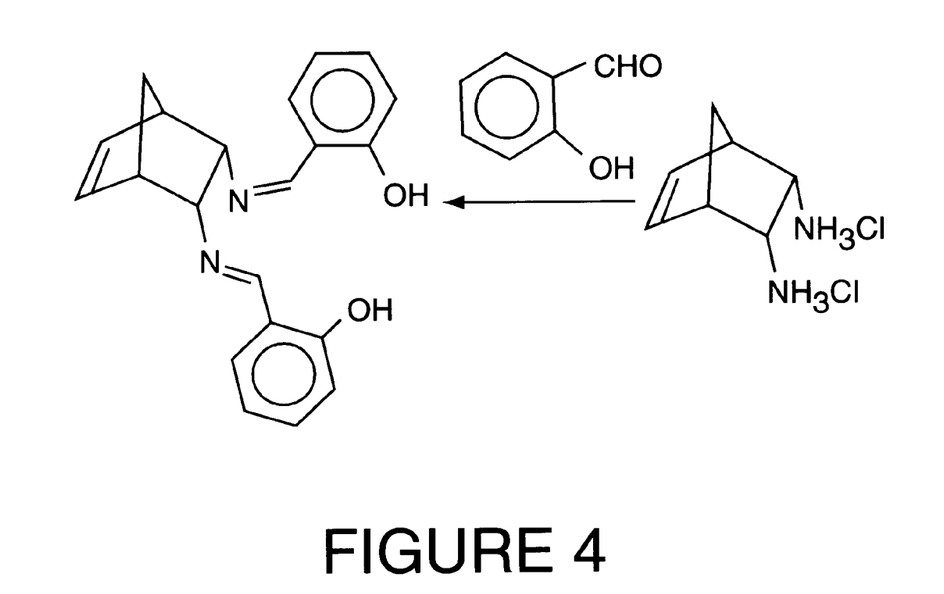
FIG. 4 depicts the formation of N,N'-disalicylidene-cis-endo-bicyclo[2.2.1]hept-5-ene-2,3 diamine by adding salicylaldehyde to compound 2.

The new family of rigid bifunctional chelating agents of the present invention also includes ligands wherein the amine nitrogen can include moieties other than acetic acid. For example, FIG. 4 below shows the formation of N,N'-disalicylidene-cis-endo-bicyclo[2.2.1]hept-5-ene-2,3 diamine by adding salicylaldehyde to compound 2.

Other useful moieties which could be attached to the amine nitrogen position include 2-mercapto ethyl groups, 2-mercaptoacetyl groups, and 2-butanon-3yl oxime.

Figure 5:
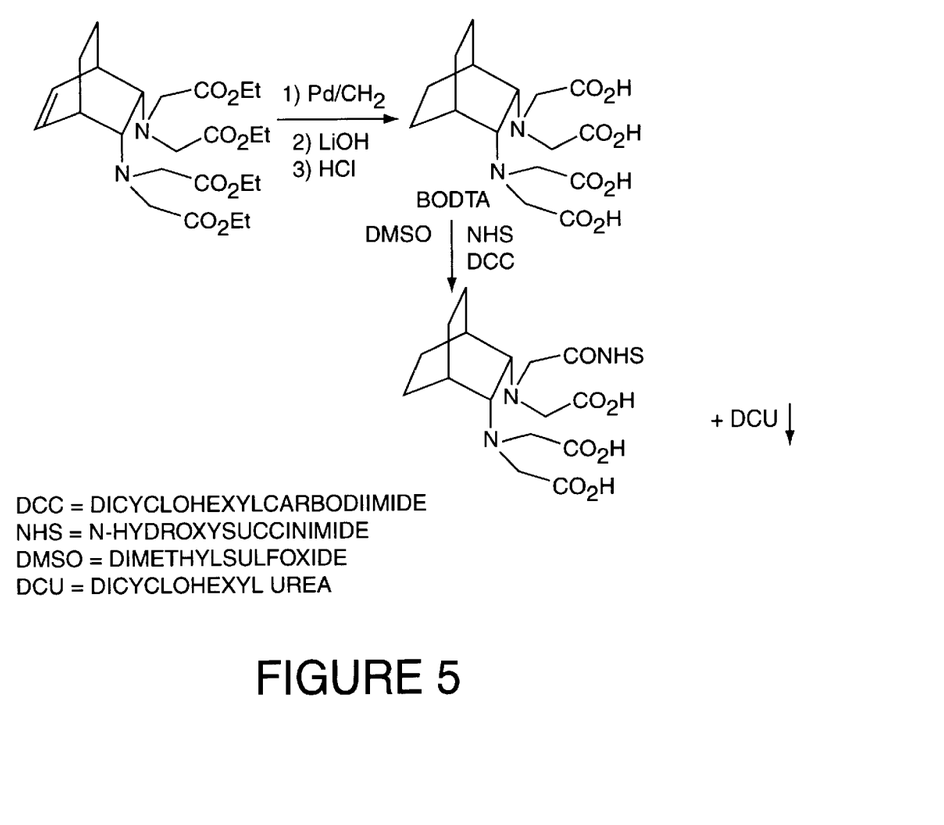
FIG. 5 depicts the derivatization of a carboxylic acid resulting in ester formation at the carboxylic acid.

The chelating agents of the present invention can be attached to proteins and other bioactive molecules by functionalizing one of the carboxylic acids or by introducing a suitable functionality at C-5 double bond. For example, an average of one carboxylic acid on the amine nitrogen can be derivatized to an activated NHS ester. The activated ester is capable of reacting with either an amine r a sulfhydryl group present on a biological binding agent. The derivatization is shown in FIG. 5 below:

Derivatization of a carboxylic acid resulting in ester formation at the carboxylic acid site may be achieved using, for example,-one molar equivalent of BODTA or BHDTA and 0.8 equivalent dicyclohexylcarbodiimide and N-hydroxysuccinimide in a solvent such as dimethyl sulfoxide (DMSO). This solution may be stored for extended periods of time, e.g. up to two months at or more 0° C., without loss of reactivity.

Figure 6:
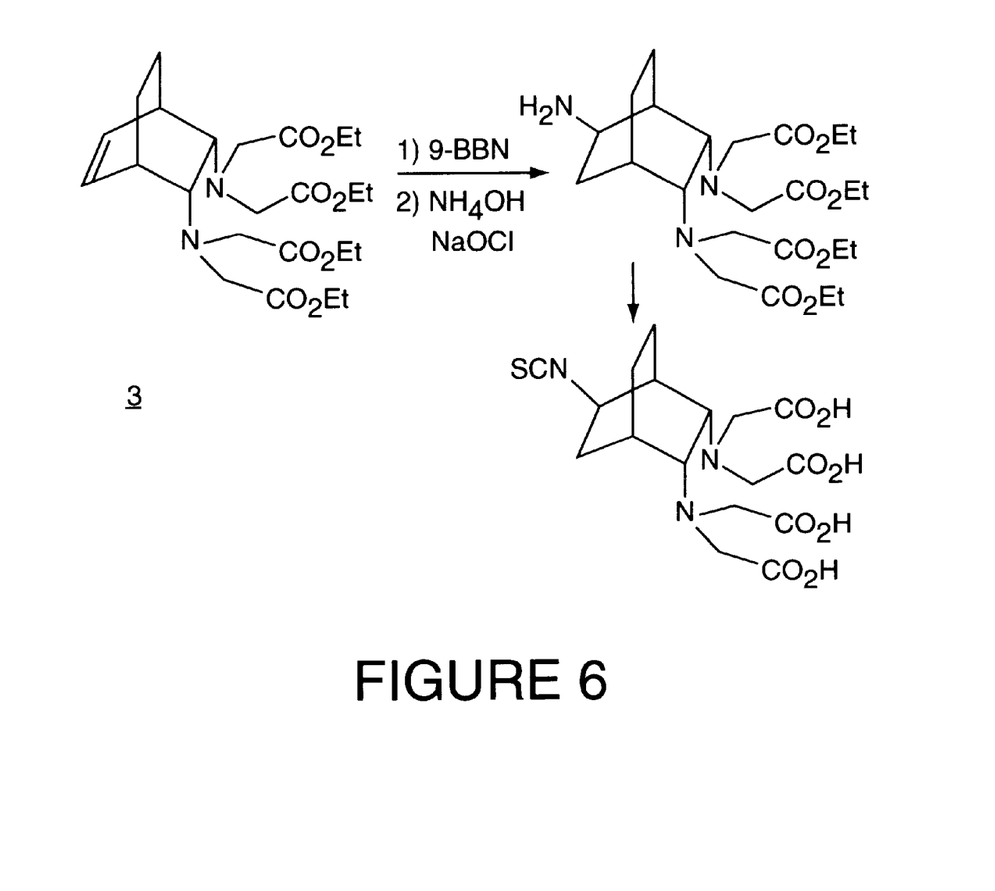
FIG. 6 depicts the hydroboration-amination sequence.

The chelating agents of the present invention can also be attached to proteins by introducing a suitable functionality at the C-5 double bond. Suitable functionalities include derivatives of amines, such as isothiocyanates, bromoacetamides or maleimides. A hydroboration-amination sequence is used to functionalize the C-5 double bond. The sequence includes reacting compound 3 with a solution of 9-borabicyclo[3.3.1] nonane (9-BBN), ammonium hydroxide and bleach. An isothiocyanate moiety can then be introduced by hydrolyzing the amine bearing ester with hydrochloric acid followed by reacting the resulting product with thiophosgene. Bromoacetamides can be introduced by the reaction of bromoacetyl bromide with the exo-amine. Maleimides are formed by the reaction of maleic anhydride with the exo-amine. The hydroboration-amination sequence described above is shown in FIG. 6 below. These sequences will also work starting with compound 14. An alternative to the hydroboration-amination functionalization of the double bond is a palladium catalyzed addition of para-iodoacetanilide and formic acid to the double bond of 3. This reaction is specific to bicyclic olefins. Hydrolysis with 3M hydrochloric acid will remove the protecting groups and the resulting aryl amine an be reacted with thiophosgene to provide the isothiocyanate.

The ligands, i.e., the chelating agents, can be conjugated to biological binding agents. Biological binding agents to which the chelating agents can be conjugated include substances capable of localizing in vitro or in vivo to a tumor or neoplasia. Neoplasia may occur, for example, in animals such as mammals including humans. Neoplasia is progressive, uncontrolled cell division which, if progeny cells remain localized, at least initially, results in the formation of an abnormal growth called a tumor or neoplasm. A neoplasm may be malignant or benign. A malignant neoplasm invades adjacent tissues and may metastasize. A neoplastic growth is generally considered to be a non-inflammatory mass formed by the growth of new cells and having no physiologic function. The conjugated radiometal chelates of the invention can be formulated per se in pharmaceutical preparation or formulated in the form of pharmaceutically acceptable salts. These preparations can be prepared according to conventional chemical methods. Radionuclides have been used for the detection and/or selective destruction of tumors localized through the use of monoclonal antibodies.

The derivatized BODTA or BHDTA chelating agents can be conjugated with various biological binding agents for localizing to a desired area. The biological binding agents may include antibodies (polycolonal and monoclonal), antibody fragments, e.g. the F(ab')$_2$, or Fab' portions of an immunoglobulin Ig, other proteins, protein fragments or peptides, genetically engineered proteins, peptides and antibodies, single chain antibodies, small molecular recognition units, polysaccharides, nucleic acids, steroids, enzymes, drugs, vitamins, and a number of other biologically active compounds.

The method of the invention has been found to be significantly superior to common methods previously used in the art for labeling antibodies using other functionalized polyaminocarboxylates such as diethylenetriaminepentaacetic acid dianhydride (DTPA-DA).

Radiometals can be complexed with the chelating agent-biological binding agent conjugates. Based on various criteria such as imaging photons, particle emission, dosimetry, and feasibility of production, a number of radiometals are considered suitable for labeling antibodies for radioimmunoimaging (RII) and/or radioimmunotherapy (RIT) (Mausner and Srivastava, Med. Phys. 20, 503–509, 1993). Examples of suitable radiometals are: $^{55}$Co, $^{64}$Cu, $^{66}$Ga, $^{68}$Ga, $^{97}$Ru, $^{99m}$Tc, $^{111}$In, and $^{203}$Pb for imaging, and $^{47}$Sc, $^{67}$Cu, $^{90}$Y, $^{105}$Rh, $^{109}$Pd, $^{153}$Sm, $^{177}$Lu, $^{186}$Re, $^{188}$Re, $^{199}$Au, and $^{212}$Bi for radiotherapy. While the chelating agents of this invention will produce more stable complexes with most of the above radiometals, $^{55}$Co, $^{64}$CU, $^{47}$SC, $^{67}$CU, $^{111}$In, $^{203}$Pb, $^{90}$Y, and $^{153}$Sm are best suited to complex with the ligands of the present invention. The improved complex formation results because of coordination geometries, and because the preferred radiometals require bifunctional chelating agents which bind the radiometal with a higher denticity, i.e., number of coordination sites and/or incorporate greater structural rigidity. The preferred complexes provide immunoconjugates with better in-vivo kinetic stability.

The chelates of the present invention can also be used in Emission Tomography to measure physiological function of organs and related biochemical processes in both health and disease. The two modes of emission tomography are single-photon emission computed tomography (SPECT) and positron emission tomography (PET). SPECT uses radionuclides that emit a single photon of a given energy and these include gamma ray emitters such as $^{67}$Ga, $^{97}$Ru, $^{99m}$Tc, $^{111}$In, $^{123}$I, $^{131}$I, $^{203}$Pb, and others. PET uses radionuclides known as positron emitters such as $^{11}$C, $^{15}$O, $^{18}$F, $^{55}$Co, $^{64}$Cu, $^{68}$Ga, $^{75}$Br, $^{89}$Zr, $^{124}$I, and others for coincidence detection in which the positron and electron annihilate each other to form two photons at 180° angle from each other. In SPECT and PET, transverse section reconstruction of the radionuclide distribution within the body is obtained by acquiring images of multiple slices of the organ or the whole body. The chelates of the invention can be used for SPECT and PET imaging studies of the physiology, function, and biochemistry of tumors, and other organs and tissues.

Radiolabelling is accomplished by incubating the bioconjugate with a salt of radiometal according to methods described in U.S. Pat. No. 5,292,938 (1994) issued to R. C. Mease, L. F. Mausner and S. C. Srivastava.

The chelating agents of the present invention may also be incorporated into macrocyclic ligands such as 1,4,7,10-tetraazacyclododecane N,N',N'',N'''tetraacetic acid (DOTA) and 1,4,8,11-tetraazacyclotetradecane N,N',N'', N'''tetraacetic acid (TETA). It has been shown that incorporation of a cyclohexyl moiety into a 1,4,8,11-tetrathiocyclotetradecane increases the stability constants of binding metal to the resulting macroligand by 1.5 orders of magnitude as the result of pre-organization of the ligand [Aronne, et al. Inorg. Chem. 34, 357, (1995)]. Molecular models suggest that the pre-organization of bycyclo[2.2.2] octyl and bicyclo[2.2.1]heptyl groups should be greater than that of the cyclohexyl moieties.

Figure 7:
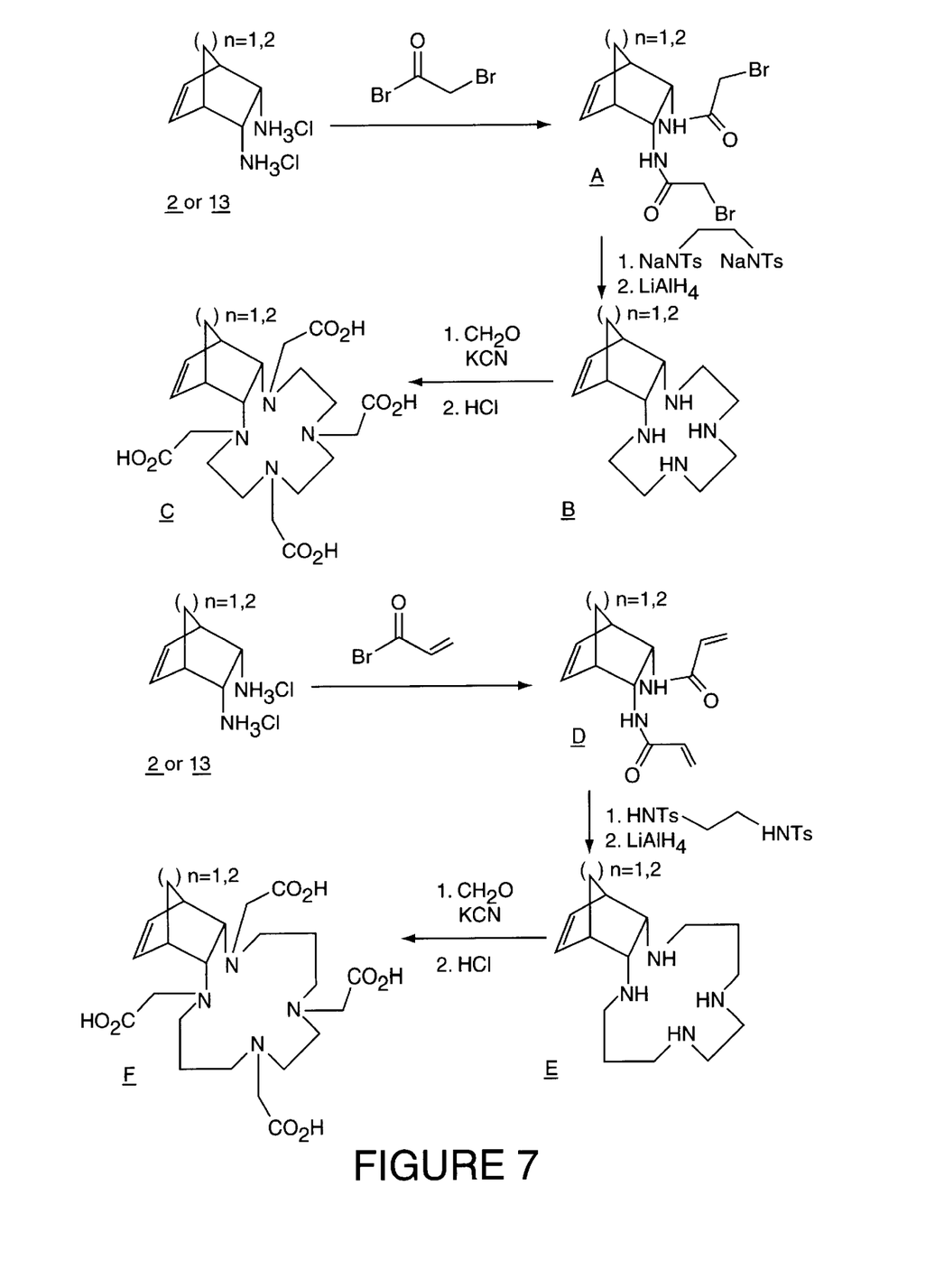
FIG. 7 depicts the syntheses of the bicyclo[2.2.2]octyl -DOTA and -TETA.

The syntheses of the bicyclo[2.2.2]octyl -DOTA and -TETA are shown in FIG. 7 below. The diamines 2 and 13 are acylated with bromoacetyl bromide to form A. Cyclization of A with disodium ditosylethylenediamine followed by lithium aluminum hydride (LAH) reduction affords the macrocycle B. Cyanomethylation followed by hydrolysis provides the bicyclo[2.2.2]-octyl DOTA and -heptyl DOTA (C). The diamines 2 and 13 are acylated with acryloyl chloride to form D. Cyclization of D with ditosylethylenediamine followed by LAH reduction provides the macrocycle E. Cyanomethylation followed by hydrolysis will provide the bicyclo[2.2.2]-octyl TETA and -heptyl TETA (F).

As a non-limiting example, one antibody system, namely an anti-carcinoma embryonic antigen antibody fragment monoclonal antibody (anti-CEA F(ab')$_2$MAb), was investigated. The anti-CEA F(ab')$_2$MAb was conjugated with BODTA, labeled with Co-57 and purified by size-exclusion high pressure liquid chromatography (HPLC). The stability of the radioconjugate in mouse serum obtained with BODTA showed a 2% loss after 48 hours. This value is enhanced by comparison to the serum stability obtained for a conventional DTPA-DA conjugate which showed an 8% loss after 48 hours.

Biodistribution studies were performed in human tumor-xenografted nude mice. As an example, $^{57}$Co labeled anti-CEA F(ab')2 immunoconjugates showed progressive improvement in biodistribution, namely, BODTANHS>DTPADA. It has been found that a $^{57}$Co BODTA immunoconjugate has a higher tumor retention than a more conventional chelating agent such as DTPADA. Moreover, the higher tumor retention time is accompanied by smaller non-target tissue uptakes. Based on these data, it can be concluded that the enhanced rigidity of the chelating agents of the present invention is an important factor which contributes to higher in-vivo stability of many radiometal immunoconjugates, and especially those of cobalt, indium, scandium and other rare earth metals.

The invention is further illustrated by the following non-limiting examples.

EXAMPLES

The following examples serve to provide further appreciation of the invention but are not meant in any way to restrict the effective scope of the invention.

The bifunctional ligands of the norbornyl type and the bicyclo[2.2.2]octyl type were obtained as shown in FIGS. 1 and 2. Procedures for obtaining the ligands of the present invention and key intermediates such as 5 norbornene-2,3-diamine (compound 2) and bicyclo[2.2.2]octyldiamine (compound 13) are described in examples 1 and 2. Example 3 provides a procedure for attaching moieties other than acetic acid to the amine nitrogen portion of the chelating agent. Examples 4 and 5 provide a serum stability and biodistribution study of an anti-CEA F(ab')$_2$Mab conjugated with BODTA.

Example 1

In this example, BODTA is synthesized according to the method illustrated in FIG. 1. All materials used in the preparation of BODTA have been synthesized as set forth below or are readily commercially available.

Preparation of 1,3-Diacetylimidazolin-2-one 1,3-Diacetylimidazolin-2-one was prepared as shown in FIG. 3 hereinabove. 1,2-Diacetylimidazolin-2-one is synthesized by reacting α-aminoacetaldehyde diethyl acetal ith potassium cyanate followed by acid-catalyzed cyclization and acylation with acetic anhydride.

A solution of cold 5N HCl (152 ml, 0.766 mole) kept at −40° C. was added to 100.00 g (0.75081 mole) of α-aminoacetaldehyde diethyl acetal maintained at reduced temperature in an ice bath. A solution of 91.49 g (1.128 mole) of potassium cyanate in 200 ml of distilled water was added slowly to the α-aminoacetaldehyde diethyl acetal solution. The resulting solution was heated at reflux for 3 hours and then allowed to cool to room temperature. The cooled solution was then concentrated under reduced pressure. The resulting solid urea was removed by filtration. The filtrate was extracted with dry chloroform, and then concentrated under reduced pressure yielding an additional 4.6 g of urea. The urea product was added to 2.0 liters of 0.10N $H_2SO_4$ and stirred at room temperature for 48 hours. 15.33 g of barium oxide (99.97 mmol) was added and the resulting solid $BaSO_4$ was removed by filtration and washed with water. Concentration of the filtrate followed by filtration yielded 45.05 g which is a 71.40% yield of imidozolin-2-one, as a white solid having the following dentification data: $^1$H NMR (DMSO-d$_6$, 60 MHz) 610.8 (bs, 2H), 6.3 (s, 2 H).

A mixture of 24.93 g (0.2965 mole) of imidozolin-2-one, 175 ml (189 g, 1.85 mole) of acetic anhydride and 8.7 ml (13 g, 0.11 mole) of trifluoroacetic acid was heated at reflux for 6 hours. The resulting solution was concentrated in vacuo. The residue was dissolved in 100 ml of methylene chloride (CH$_2$Cl$_2$) and then filtered. After the solvent had been removed under reduced pressure, the resulting oil was passed through a plug of silica gel using chloroform. The solvent was removed under reduced pressure leaving 42.7 g (0.254 mole, 85.6% yield) of a yellow solid having a melting point of 101–103° C. The compound was identified as 1,3 diacetylimidazolin-2-one. The identification data is shown below:

$^1$H NMR (CDCl$_3$) δ 7.08 (s, 2H), 2.65 (s, 6H); IR (Nujol) 1760, 1735, 1710 cm$^{-1}$. Anal. Calcd for C$_7$H$_8$N$_2$O$_3$: C, 50.00; H, 4.79; N, 16.66. Found: C, 50.08; H, 4.85; N, 16.58.

Preparation of 3,5-Diacetyl-3,5-diazatricyclo[5.2.2.0] undec-8-en-4-one (1)

A mixture of 15.0 g (89.2 mmol) of 1,3-diacetylimidazolin-2-one, 12.5 g (0.156 mole) of 1,3-cyclohexandiene and 60 ml of dry, distilled xylene was heated at 170° C. in a Wheaton pressure bomb for 48 hours. The resulting mixture was allowed to cool to room temperature. Filtration followed by washing with ethyl acetate generated 12.35 g (49.74 mmol, 55.8%) of 3,5-diacetyl-3, 5-diazatricyclo[5.2.2.0]undec-8-en-4-one as a white solid. Column chromatography (1:1 EtOAc/hexanes on silica gel) used to separate the residue from the filtrate afforded an additional 4.70 g of the product. The total weight of the product was 17.05 g (68.67 mmol, 77.0% yield). The product was a white solid having a melting point of 186–191° C. Its identification data is shown below:

$^1$H NMR (CDCl$_3$) δ 6.15 (m, 2H), 4.23 (s, 2H), 3.32 (d, J=1.4 Hz, 2H), 2.48 (s, 6H), 1.56 (m, 2H), 1.31 (m, 2H); IR (KBr) 1740, 1680, 1380, 1350, 1260 cm$^{-1}$. Anal. calculated for C$_{12}$H$_{16}$N$_2$O$_3$: C, 62.89; H, 6.50; N, 11.28. Found: C, 62.97; H, 6.51; 11.34.

Preparation of 3,5-Diazatricyclo[5.2.2.0]undec-8-en-4-one

A mixture of 5.08 g (20.5 mmol) of 3,5-diacetyl-3,5-diazatricyclo[5.2.2.0]undec-8-en-4-one, 4.00 g (61.5 mmol) of 86.2% potassium hydroxide and 61 ml of methanol was heated at reflux for 18 hours. The resulting solution was then concentrated in vacuo. Water was added and the solution was neutralized with 10% HCl. The solution was extracted with CH$_2$Cl$_2$, then dried with MgSO$_4$, and concentrated under reduced pressure. 2.83 g (17.2 mmol, 84.2% yield) of 3,5-diazatricyclo[5.2.2.0]undec-8-en-4-one was produced as a white solid having a melting point of 225–233° C. The product had the following identification data:

$^1$H NMR (CDCl$_3$) δ 6.24 (t, J=4 Hz, 2H), 5.00 (s, 2H), 3.87 (s, 2H), 2.65 (s, 2H), 1.43 (m, 2H), 1.26 (m, 2H); IR (KBr) 3220, 2920, 1670 cm$^{-1}$. Anal. Calculated for C$_9$H$_{12}$N$_2$O: C, 65.83; H, 7.37; N, 17.06. Found: C, 65.94; H, 7.36; 17.11.

Preparation of cis-endo-Bicyclo[2.2.2]oct-5-ene-2,3-diamine Dihydrochloride (2)

A slurry of 5.70 g (34.7 mmol) of 3,5-diazatricyclo [5.2.2.0]undec-8-en-4-one, 22.4 g (0.348 mole) of 87.1% potassium hydroxide, 35 ml of methanol and 22 ml of distilled water was heated at 170° C. in a bomb for 113 hours. The solvent of the resulting solution was removed under reduced pressure. Water was added and the resulting solution was continuously extracted with CH$_2$Cl$_2$. The organic layer was concentrated in vacuo. Absolute ethanol (110 ml) was added to the residue and HCl gas was bubbled through the ethanolic solution. On cooling of the solution, a white solid formed. The white solid was isolated by filtration, washed with $CH_2Cl_2$ and dried under vacuum. This solid (5.30 g, 25.1 mmol, 72.3% yield) was cis-endo-bicyclo[2.2.2]oct-5-ene-2,3-diamine dihydrochloride (2) having the following identification data:

$^1$H NMR (DMSO-$d_6$) δ 8.43 (bs, 6H), 6.32 (t, J=4 Hz, 2H), 3.69 (s, 2H), 2.93 (s, 2H), 1.59 (d, J=8 Hz, 2H), 1.18 (d, J=8 Hz, 2H). Anal. Calculated for $C_8H_{16}N_2Cl_2$: C, 45.51; H, 7.64, N, 13.18. Found: C, 45.43; H, 7.68; N, 13.15.

Preparation of cis-Tetraethyl Bicyclo[2.2.2]oct-5-ene-2,3-diamine-N,N,N',N'-tetraacetate (3)

A slurry of the diamine cis-endo-bicyclo[2.2.2]oct-5-ene-2,3-diamine dihydrochloride (2.61 g, 12.4 mmol), potassium carbonate (15.24 g, 110.3 mmol), ethyl iodoacetate (9.0 ml, 16 g, 76 mmol) and dry, distilled dimethylformamide was heated at 80° C. for 90 hours. The resulting mixture was filtered and the solid was washed with EtOAc. The filtrate was concentrated under reduced pressure. A tan solid was formed, which was partitioned between water and $CH_2Cl_2$. The organic extracts were dried with $Na_2SO_4$, filtered and concentrated in vacuo. Column chromatography (1:1 EtOAc/hexanes on $SiO_2$) on the resulting red oil produced a yellow oil (4.75 g, 9.84 mmol, 79.6% yield) having the following identification data:

$^1$H NMR (CDCl$_3$) δ 6.17 (dd, J=4 and 3 Hz, 2H), 4.12 (g, J=7 Hz, 8H), 3.76 (s, 8H), 3.22 (s, 2H), 2.70 (s, 2H), 1.25 (m, 16H). Anal. Calculated for $C_{24}H_{38}N_2O_8$: C, 59.73; H, 7.94; N, 5.81. Found: C, 59.57; H, 7.97; N, 5.76.

Preparation of cis-Bicyclo[2.2.2]oct-5-ene-2,3-diamine-N,N,N',N'-tetraacetic acid (4)

3M HCl in Super Q water (50 ml) was added to a solution of cis-tetraethyl bicyclo[2.2.2]oct-5-ene-2,3-diamine-N,N,N',N'-tetraacetate (0.36 g, 0.75 mmol) in absolute ethanol (10 ml). The resulting mixture was heated in a 110° C. 20 oil bath for 8 hours. The resulting mixture was then allowed to cool to room temperature and then concentrated under reduced pressure. A tan solid was left which weighed 0.27 g (0.73 mmol, 98% yield) after drying under vacuum. The cis-bicyclo[2.2.2]oct-5-ene-2,3-diamine-N,N,N',N'-tetraacetic acid had the following identification data:

$^1$H NMR (D$_2$O) d 6.37 (m, 2 H), 3.88 (m, 8 H), 3.75 (s, 2 H), 3.14 (s, 2 H), 1.58 (d, J=8 Hz, 2 H), 1.33 (d, J=8 Hz, 2 H). Anal calculated for $C_{16}H_{22}N_2O_8 \cdot HCl \cdot \frac{1}{2} H_2O$: C, 46.22; H, 5.82; N, 6.74. Found: C, 46.33; H, 5.72; N, 6.73.

Preparation of cis-Bicyclo[2.2.2]octane-2,3-diamine-N,N,N',N'-tetraacetic acid (5)

A slurry of cis-bicyclo[2.2.2]oct 5-ene-2,3-diamine-N,N,N',N'-tetraacetic acid (compound 4) (0.1080 g. 0.2916 mmol), palladium on carbon (10%, 10.8 mg) and absolute ethanol (10 ml) was hydrogenated at 5 psig. The resulting mixture was filtered through a glass-fiber filter and the filter was washed with absolute ethanol. The filtrate was concentrated under reduced pressure leaving cis-bicyclo[2.2.2] octane 2,3-diamine-N,N,N',N'-tetraacetic acid (BODTA) (0.1049 g, 0.2817 mmol, 96.60% yield) having the following identification data:

$^1$H NMR (D$_2$O) δ 4.09 (m, 4H), 3.72 (m, 6H), 2.11 (m, 2H), 1.57 (m, 8H). IR (KBr) 3423, 2956, 2879, 1736 cm$^{-1}$.

Example 1 shows that the method of the present invention is simple, efficient and results in a high overall yield of BODTA of over 35%.

Example 2

In this Example, BHDTA is synthesized according to the method illustrated in FIG. 2 hereinabove. All materials used in the preparation of BHDTA have been synthesized as set forth below or are readily commercially available.

Preparation of 3,5-Diacetyl-3,5-diazatricyclo[5.2.1.0]dec-8-en-4-one (11)

A mixture of 3.34 g (19.9 mmol) of 1,3-diacetylimidazolin-2-one as prepared in Example 1, 1.40 ml (1.38 g, 10.4 mmol) of dicyclopentadiene and 20.0 ml of dry, distilled xylene was heated at 180° C. under nitrogen in a sealed tube for 90 hours. The solvent was removed in vacuo. The reaction of 1,3-diacetylimidazolin-2-one with cyclopentadiene provided product (11) and another Diels-Alder adduct, 5,7-diacetyl-5,7-diazapentacyclo[9.2.1.1.0.0] pentadec-12-en-6-one. Column chromatography was used to separate the two Diels-Alder adducts. Thus, column chromatography (25% EtOAc/hexanes on silica gel) afforded 2.04 g (8.71 mmol, 43.8%) of 5,7-diacetyl-5,7-diazapentacyclo[9.2.1.1.0.0]pentadec-12-en-6-one as a white solid and 3,5-diacetyl-3,5-diazatricyclo[5.2.1.0]dec-8-en-4-one as a white solid. For 5,7-diacetyl-5,7-diazapentacyclo [9.2.1.1.0.0]pentadec-12-en-6-one the identification date is shown below: $^1$H NMR (CDCl$_3$) δ 6.00 (m, 2H), 4.07 (t, J=2 Hz, 2H), 3.0 to 1.8 (bm, 6H), 2.56 (s, 6H), 1.5 to 0.5 (bm, 4H).

For 3,5-diacetyl-3,5-diazatricyclo[5.2.1.0]dec-8-en-4-one the identification date is shown below: mp 107–112° C., $^1$H NMR δ 6.04 (t, J=1.8 Hz, 2H), 4.42 (t, J=1.7 Hz, 2H), 3.53 (t, J=1.7 Hz, 2H), 2.47 (s, 6H), 1.69 (dt, J=9.8 and 1.8 Hz, 1H), 1.39 (d, J=9.8 Hz, 1H); IR (KBr) 3000, 1780, 1750, 1695, 1380, 1280, 1240 cm$^{-1}$. Anal. Calculated for $C_{12}H_{14}N_2O_3$: C, 61.52; H, 6.02; N, 11.96. Found: C, 61.54; H, 6.07; N, 11.82.

Preparation of 3,5-Diazatricyclo[5.2.1.0]dec-8-en-4-one (12)

A mixture of 1.88 g (8.03 mmol) of the 3,5 diacetyl-3,5-diazatricyclo[5.2.1.9]dec-8-en-4-one (11), 1.55 g (24.2 mmol) of 86.2% potassium hydroxide, 40 ml of methanol were heated at reflux for 48 hours. The resulting solution was allowed to cool to room temperature and then neutralized with 3M HCl solution. The solution was extracted with $CH_2Cl_2$, then dried with MgSO$_4$ and concentrated in vacuo producing 1.10 g (7.32 mmol, 91.3% yield) of a white solid having the identification data shown below:

$^1$H NMR (CDCl$_3$) δ 6.16 (t, J=1.8 Hz, 2H), 5.24 (bs, 2H), 4.13 (s, 2H), 3.04 (t, J=1.5 Hz, 2H), 1.56 (dt, J=9.4 and 1.8 Hz, 1H), 1.18 (d, J=9.4 Hz, 1H); IR (KBr) 3250, 2960, 1680, 1450 cm$^{-1}$.

Preparation of cis-endo-Bicyclo[2.2.1]hept-5-ene-2,3-diamine Dihydrochloride (13)

A mixture of 4.76 g (31.7 mmol) of 3,5-diazatricyclo [5.2.1.0]dec-8-en-4-one (12), 20.63 g (0.3169 mole) of 86.2% potassium hydroxide, 30 ml of methanol and 20 ml of water was heated at 170° C. in a Teflon-lined bomb for 90 hours. The solvent was then removed under reduced pressure. Water was added and the resulting solution was continuously extracted with chloroform. The organic phase was concentrated in vacuo. The residue was dissolved in 50 ml of absolute ethanol and HCl gas was bubbled through the solution. Concentration of the resulting solution under reduced pressure generated 3.64 g (18.5 mmol, 58.3% yield) of cis-endo-bicyclo[2.2.1]hept-5-ene-2,3-diamine dihydrochloride as a brown solid having the identification data shown below:

$^1$H NMR (DMSO-d$_6$) δ 8.40 (bs, 6H), 6.34 (s, 2H), 3.95 (s, 2H), 3.18 (s, 2H), 1.57 (d, J=9.5 Hz, 1H), 1.53 (d, J=9.5 Hz, 1H); IR (KBr) 3480, 3000, 1570 cm$^{-1}$.

Preparation of cis-tetraethyl bicyclo[2.2.1]hept-5-ene-2,3-diamine-N,N,N',N'-tetraacetate (14)

A slurry of cis-endo-bicyclo[2.2.1]hept-5-ene-2,3-diamine dihydrochloride (0.90 g, 4.6 mmol) (13), potassium carbonate (6.3 g, 46 mmol), ethyl iodoacetate (4.3 ml, 1.8 g, 36 mmol) and dry, distilled DMF (100 ml) are heated at 65° C. for about 24 hours. The resulting solution is filtered and the solid is washed with EtOAc. The filtrate is concentrated under reduced pressure leaving a sticky solid, which is partitioned between water and CH$_2$Cl$_2$. The organic extracts are dried with MgSO$_4$, filtered and concentrated in vacuo. Column chromatography (4:1 hexanes/EtOAc on SiO$_2$) afforded a yellow oil (1.62 g, 3.46 mmol, 76% yield) having the identification data shown below:

$^1$H NMR (CDCl$_3$) δ 6.15 (bs, 2H), 4.12 (m, 8H), 3.76 (m, 8H), 3.61 (s, 2H), 2.97 (bs, 2H), 1.25 (m, 14H). IR (neat) 1730 and 1660 cm$^{-1}$.

Preparation of cis-bicyclo[2.2.1]hept-5-ene-2,3-diamine-N,N,N',N'-tetraacetic acid Cis-tetraethyl-bicyclo[2.2.1]hept-5-ene-2,3-diamine-N,N,N',N'-tetraacetate (0.4257 g, 0.9086 mmol) was refluxed in 3.0M HCl in Super Q water for 18 hours. The resulting solution was filtered. The filtrate was concentrated under reduced pressure leaving a brown solid (0.3150 g, 0.8840 mmol, 97.29% yield), which was cis-bicyclo[2.2.1]hept-5-ene-2,3-diamine-N,N,N',N'-tetraacetic acid having the following identification data:

$^1$H NMR (D$_2$O) δ 6.36 (s, 2H), 4.05 (m, 8H), 3.35 (s, 2H), 3.28 (s, 2H), 1.73 (d, J=9 Hz, 1H), 1.47 (d, J=9 Hz, 1H). IR (KBr) 3388, 3016, 1760, 1736 cm$^{-1}$.

Preparation of cis-bicyclo[2.2.1]heptane-2,3-diamine-N,N,N',N'-tetraacetic acid (15)

A slurry of cic-bicyclo[2.2.1]hept-5-ene-2,3-diamine-N,N,N',N'-tetraacetic acid (0.1080 g, 0.2916 mmol), absolute ethanol (10 mL) and 10% palladium on carbon (10.8 mg) was hydrogenated at 5 psig. After purging with nitrogen, the resulting solution was filtered through a glass fiber filter. The catalyst was washed with absolute ethanol. The filtrate was concentrated under reduced pressure leaving a white solid (0.1049 g, 0.2817 mmol, 96.60% yield), which was cis-bicyclo[2.2.1]heptane-2,3-diamine-N,N,N',N'-tetraacetic acid having the following identification data:

$^1$H NMR (D$_2$O) δ 4.02 (m, 8H), 2.73 (s, 2H), 1.70 (m, 2H), 1.54 (m, 4H), 1.30 (m, 2H). IR (KBr) 4325, 3106, 1758, 1737 cm$^{-1}$.

Example 2 shows that the method of the present invention is simple, efficient and results in a high yield of BHDTA of over 17%.

Example 3

In this example, moieties other than acetic acid are attached to the amine nitrogen position of the chelating agents provided by the present invention. The resulting rigid structure is also useful for preparing stable radiometal conjugates with many biologically active molecules.

Preparation of N,N'-Disalicylidene-cis-endo-bicyclo[2.2.1]hept-5-ene-2,3-diamine Lithium hydroxide (0.0438 g, 1.04 mmol) was added to a slurry of 0.0989 g (0.502 mmol) of cis-endo-bicyclo[2.2.1]hept-5-ene-2,3-diamine dihydrochloride (13). The reaction was stirred for 15 minutes until all of cis-endo-bicyclo[2.2.1]hept-5-ene-2,3-diamine dihydrochloride had dissolved. Salicylaldehyde (0.13 ml, 0.15 g, 1.2 mmol) was added and the reaction solution was stirred for 1 hour at room temperature. On cooling to −20° C., a yellow precipitate formed. The solid was isolated by filtration and washed with cold absolute ethanol. The solid was dissolved in ether and the resulting solution was then filtered. Concentration of the filtrate afforded 0.1138 g (0.3424 mmol, 68.6% yield) of N,N'-disalicylidene-cis-endo-bicyclo[2.2.1]hept-5-ene-2,3-diamine as a yellow solid having the following identification date:

$^1$H NMR (CDCl$_3$) δ 10.87 (s, 2H), 8.36 (s, 2H), 7.16 (m, 4H), 6.92 (d, J=8.3 Hz, 2H), 6.78 (t, J=7.4 Hz, 2H), 6.45 (s, 2H), 4.21 (s, 2H), 3.11 (5, 2H), 1.70 (s, 2H).

Example 4

In this example, the serum stability of radiometal conjugates of BODTA was determined and compared to a control ligand such as DTPADA.

An anti CEA F(ab')$_2$MAb was conjugated with an average of 0.6 BODTA per MAb molecule through one of the carboxylate groups, labelled with Co-57 and purified by size-exclusion HPLC. The labeled conjugates were incubated in mouse serum at 37° C. for up to 4 days. Aliquots were removed, injected onto a Zorbax GF-250 HPLC column and eluted with 0.1M phosphate buffer at pH 7.0, at a flow rate of 1 ml/min and with a detector setting at 280 nm. The retention time for F(ab')$_2$ immunoconjugate was 8.3 minutes and 10.6 minutes for the metal complexes. These values indicate that the labeled F(ab')$_2$ immunoconjugate retains 98% activity after 48 hours compared to only 2% activity for free metal complexes.

Additionally, the stability of the resulting radioconjugate in mouse serum was measured at a 48 hour interval and the value was also compared to that of a conventional conjugate such at DTPADA. It has been found that the stability of the $^{57}$Co radioimmunoconjugate showed only a 2% loss which is significantly better than the stability of conventional DTPADA conjugate which showed an 8% loss.

Example 5

In this example, the biodistribution of $^{57}$Co labeled conjugates of BODTA anti-CEA F(ab')$_2$ in human tumor xenografted nude mice was measured and compared to values obtained for a conventional conjugate such as DTPADA.

For conjugation with monoclonal antibodies, an average of one COOH group of unsaturated BODTA was converted into an NHS ester using 0.8 equivalent of dicyclohexylcarbodiamide (DCC). An anti-CEA F(ab')$_2$MAb was conjugated with an average of 0.6 BODTA per MAb molecule, labeled with Co-57 and then purified by size-exclusion HPLC. Biodistribution studies were performed in tumor xenografted nude mice where the tumor cells were LS-174T cancer cells of human origin. The results are shown in Table 1 below.

TABLE 1

Biodistribution of $^{57}$Co labeled conjugates of anti-CEA
F(ab'), in nude tumor mice (LS-174T tumor xenografts)*

| Conjugates | Time (h) | % ID per g | | | | Whole body retention |
| --- | --- | --- | --- | --- | --- | --- |
| | | Tumor | Blood | Liver | Kidney | (% ID) |
| DTPA-DA | 24 | 13.59 ± 1.32 — | 2.50 ± 0.46 (5.4) | 5.03 ± 0.58 (2.7) | 2.92 ± 0.38 (4.6) | 48 ± 3 |
| | 48 | 6.86 ± 0.58 — | 0.49 ± 0.03 (13.9) | 3.00 ± 0.21 (2.3 | 1.74 ± 0.16 (3.9) | 23 ± 1 |
| BODTA-NHS | 24 | 21.55 ± 2.74 — | 4.41 ± 0.17 (4.9) | 4.83 ± 0.16 (4.5) | 5.98 ± 0.44 (3.6) | 57 ± 3 |
| | 48 | 11.63 ± 2.04 — | 0.65 ± 0.18 (18.0) | 2.36 ± 0.27 (4.9) | 2.17 ± 0.41 (5.4) | 28 ± 3 |

*Tumor to tissue ratios are given in parentheses

Table 1 illustrates tissue distribution of $^{57}$Co immunoconjugates in mice at 24 hours and 48 hours. The results show that the more rigid BODTA forms an immunoconjugate with $^{57}$Co which has a higher tumor retention than DTPADA. This result is achieved both after 24 hours and 48 hours. Moreover, the higher tumor retention time is accompanied by fairly low non-target tissue uptakes as illustrated by tumor to tissue ratios.

Thus, while there have been described what are presently believed to be the preferred embodiments of the present invention, those skilled in the art will realize that other and further modifications can be made without departing from the true spirit of the invention, and it is intended to include all such modifications and variations as come within the scope of the claims as appended herein.

What is claimed is:

1. A detectably labeled biconjugate compound which comprises:

a monoclonal antibody; and a Tc-99m chelate coupled to said monoclonal antibody, wherein said Tc-99m chelate includes Tc-99m coupled to a chelating agent of the formula wherein X is hydrogen and Y is —OH.

* * * * *